United States Patent [19]

Doss et al.

[11] Patent Number: 4,651,734
[45] Date of Patent: Mar. 24, 1987

[54] ELECTROSURGICAL DEVICE FOR BOTH MECHANICAL CUTTING AND COAGULATION OF BLEEDING

[75] Inventors: James D. Doss; Charles W. McCabe, both of Los Alamos, N. Mex.

[73] Assignee: The United States of America as represented by the United States Department of Energy, Washington, D.C.

[21] Appl. No.: 699,888

[22] Filed: Feb. 8, 1985

[51] Int. Cl.[4] ............................................. A61B 17/36
[52] U.S. Cl. .......................... 128/303.14; 128/303.17
[58] Field of Search ...................... 128/303.14, 303.17, 128/800

[56] References Cited

U.S. PATENT DOCUMENTS

| | | |
|---|---|---|
| 3,768,482 | 10/1973 | Shaw ............................. 128/303.14 |
| 3,826,263 | 7/1974 | Cage et al. ..................... 128/303.14 |
| 3,885,569 | 5/1975 | Judson ............................ 128/303.14 |
| 4,161,950 | 7/1979 | Doss et al. ..................... 128/303.14 |
| 4,228,800 | 10/1980 | Degler, Jr. et al. ............. 128/303.14 |
| 4,273,127 | 6/1981 | Auth et al. ..................... 128/303.14 |
| 4,353,371 | 10/1982 | Cosman ......................... 128/303.17 |
| 4,375,218 | 3/1983 | DiGeronimo .................. 128/303.17 |
| 4,512,343 | 4/1985 | Falk et al. ...................... 128/303.17 |

Primary Examiner—Edward M. Coven
Assistant Examiner—Randy Citrin
Attorney, Agent, or Firm—Samuel M. Freund

[57] ABSTRACT

Bipolar electrical coagulation of tissue using radio-frequency energy is combined with the functions of conventional surgical pressure tissue cutting instruments without significant modification thereof in a single instrument with the result that a surgeon can perform both procedures without having to redirect his attention from the area of the surgery.

5 Claims, 4 Drawing Figures

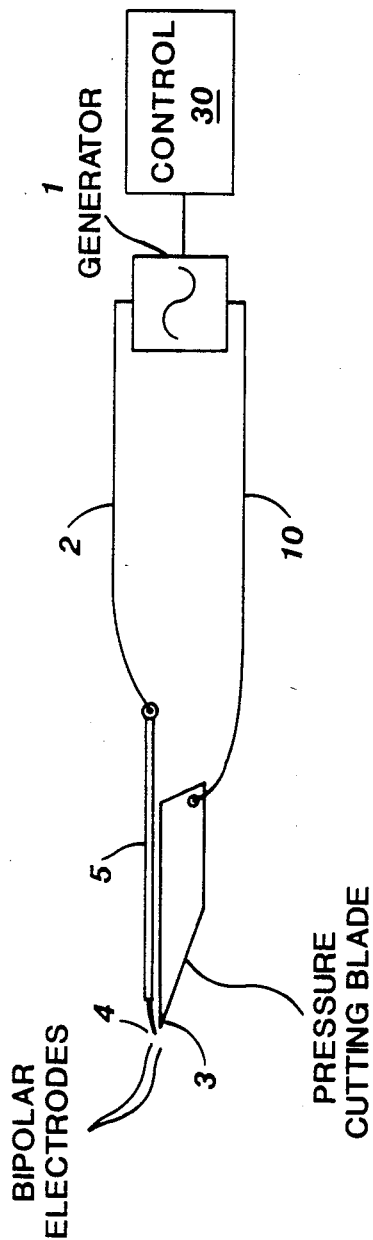
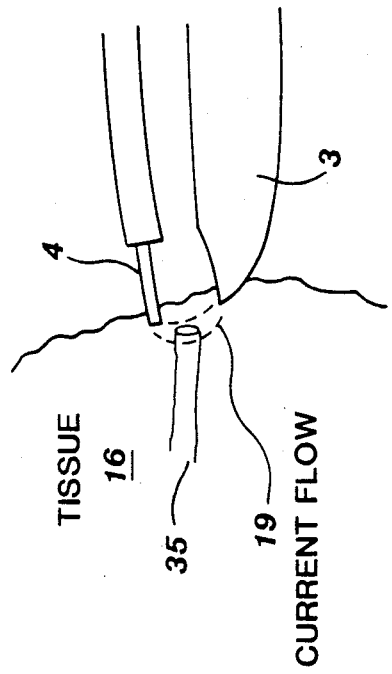

ELECTROSURGICAL DEVICE FOR BOTH MECHANICAL CUTTING AND COAGULATION OF BLEEDING

This invention is the result of a contract with the Department of Energy (Contract No. W-7405-ENG-36).

BACKGROUND OF THE INVENTION

The present invention relates generally to surgical instruments and more particularly to a combination cutting and bipolar coagulation instrument.

In surgical procedures, it is common practice to use electric currents flowing from metallic instruments to achieve coagulation of blood vessels which have been cut or ruptured as a result of the surgery. Generally, a single coagulating electrode is placed in the area to be treated, while a second electrode is connected to the patient at a position remote therefrom. This second electrode has a large surface area, and the area of contact with the patient is large in order to minimize current-induced burns. Such an apparatus is known as a monopolar electrosurgical instrument. In contrast thereto, it is also possible to place two electrodes in contact with the tissue to be coagulated, one on each side of the bleeding vessel or vessels. High frequency electric current is caused to flow between the two electrodes for a time sufficient to effectuate a localized heating which results in coagulation of the vessels. The large remote electrode is not required for the implementation of the coagulation in this latter situation. Such an apparatus is known as a bipolar electrosurgical instrument.

Great precision is required for many surgical procedures, and the surgeon often uses a single, preferred hand to operate both cutting and coagulating instruments. For example, a surgeon may first use a cutting instrument, such as a scalpel, and then exchange this instrument, when necessary, for a coagulating instrument. Prior to the present invention, the surgeon would be required to redirect his attention from the area of the incision in order to receive and prepare for the operation of the coagulation instrument. A single instrument that combined the functions of cutting and coagulating would increase a surgeon's effectiveness in essentially all surgical procedures, but of singular significance is the value of such an instrument in the area of microsurgical procedures where the surgeon views the operating field with the aid of a microscope. In the application of such procedures, an exchange of instruments is particularly distracting to the surgeon.

Several examples of monopolar and bipolar electrosurgical instruments as well as other types of combination surgical and coagulation instruments will now be briefly described to provide a background for the present invention.

1. In "Surgical Cutting Instrument Having Electrically Heated Cutting Edge," U.S. Pat. No. 3,768,482 issued to Robert F. Shaw on Oct. 30, 1973, and in "Electrically Heated Surgical Cutting Instrument," U.S. Pat. No. 3,826,263, issued to John M. Cage et al. on July 30, 1974, the inventors describe the use of instruments having electrically heated cutting edges.

2. A monopolar electrosurgical instrument which is a combination forceps and scalpel is described in "Forceps, Scalpel, and Blood Coagulating Surgical Instrument," U.S. Pat. No. 4,375,218, issued to Ernest M. DiGeronimo on Mar. 1, 1983. Coagulation is achieved by a current derived from the entire contact area of the instrument with the tissue of interest. A second electrode, which is not described, is necessary to complete the current path. A likely possibility is a large electrode located away from the region of the surgery.

3. In U.S. Pat. No. 4,273,127, "Method for Cutting and Coagulating Tissue," issued to David C. Auth et al. on June 16, 1981, the inventors teach the use of laser radiation coupled to the tissue to be simultaneously cut and coagulated by means of a scalpel-like instrument which cannot be used to pressure cut tissue.

4. A bipolar coagulating surgical instrument which can be used only for coagulating tissue is described in "Longitudinally, Side-Biting, Bipolar Coagulating, Surgical Instrument," U.S. Pat. No. 4,353,371 issued to Eric R. Cosman on Oct. 12, 1982.

5. A bipolar electrosurgical knife which utilizes high frequency electrical current passed between a plurality of closely-spaced electrodes in contact with the tissue to be simultaneously cut and coagulated is described in "Bipolar Electrosurgical Knife," U.S. Pat. No. 4,228,800 issued to Howard E. Degler, Jr. et al. on Oct. 21, 1980. As in reference 3 described hereinabove, the surgical instrument cannot be used to pressure cut tissue. A similar electrosurgical knife having only two electrodes is described in "Electro-surgical Knife," U.S. Pat. No. 4,161,950 issued to James D. Doss et al. on July 24, 1979.

SUMMARY OF THE INVENTION

Accordingly, it is an object of the present invention to provide a surgical instrument for cutting and coagulating tissue.

Another object of our invention is to provide a surgical instrument for cutting and coagulating tissue which can be attached to a conventional surgical scalpel.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus of this invention may include pressure cutting means, such as a scalpel, to take the simplest example, which serves as a first electrode and has a leading edge or a front location for its cutting edge, second electrode means set apart from and electrically insulated from the pressure cutting means, means for attaching the second electrode means to the pressure cutting means, and means for providing a voltage between the pressure cutting means and the second electrode means, whereby an electric current can be made to flow between the side opposite the cutting edge of the means for pressure cutting and the second electrode means and between the leading edge of the pressure cutting means and the second electrode means through tissue with which the two electrodes have been placed in contact, the electric current having sufficient amplitude to cause coagulation therein. Preferably, the means for applying the voltage between the electrodes includes a source of radiofrequency voltage. It is also preferred that the second electrode means is slidably attached to the pressure cutting means, whereby the position of the second electrode means can be adjusted relative to the leading edge of the pressure cutting means such that coagulation of the tissue which has just been cut by the pressure cutting means can be achieved essentially immediately thereafter.

The present invention may also comprise, in accordance with its objects and purposes, an electrode pair including first electrode and a second electrode spaced apart from and electrically insulated from each other, pressure cutting means, such as a scalpel, to take the simplest example, having a leading edge or a front location for its cutting edge and being spaced apart from and electrically insulted from the electrode pair, means for attaching the electrode pair to the pressure cutting means, and means for providing a voltage between the first electrode and the second electrode, whereby an electric current can be made to flow between the first electrode and the second electrode through tissue with which the two electrodes have been placed in contact, the electric current having sufficient amplitude to cause coagulation therein. Preferably, the means for applying the voltage between the electrodes includes a source of radio-frequency voltage. It is also preferred that the electrode pair is slidably attached to the pressure cutting means, whereby the position of the electrode pair can be adjusted relative to the leading edge of the pressure cutting means such that coagulation of the tissue which has just been cut by the pressure cutting means can be achieved essentially immediately thereafter.

Benefits and advantages of the present invention include the combination of the functions of a bipolar electric current coagulator and a pressure cutting in a single instrument in order that a surgeon may perform cutting and coagulating procedures without changing surgical instruments. Neither the cutting nor the coagulating effectiveness of the combination instrument is compromised according to the practice of the present invention over instruments which are designed to perform one or the other function exclusively. In fact, according to the teachings of the present invention, conventional surgical instruments may be easily outfitted with coagulating capability. For a given bipolar electrode size and shape there is an optimum distance between the electrodes for effective coagulation. If the distance is too small, excessive tissue damage and blood vessel rupture may occur, while if the distance is too great, insufficient electric current density in the central region between the electrodes to affect coagulation may occur. That is, the electric field strength and the resulting heating will be concentrated in the immediated vicinity of each electrode tip. The commonly-used forceps bipolar coagulator is difficult to use with substantial reproducibility since obtaining the optimum coagulation with a variable electrode spacing depends heavily on the skill and experience of the surgeon.

BRIEF DESCRIPTION OF THE DRAWINGS

The accompanying drawings, which are incorporated in and form a part of the specification, illustrate two embodiments of the present invention and, together with the description, serve to explain the principles of the invention. In the drawings:

FIG. 1 is a schematic representation of one embodiment of the apparatus of the present invention showing the use of a pressure cutting member as one electrode.

FIG. 2 schematically shows the use of the apparatus of the present invention shown in FIG. 1 for coagulating tissue.

DETAILED DESCRIPTION OF THE INVENTION

Figure 3:
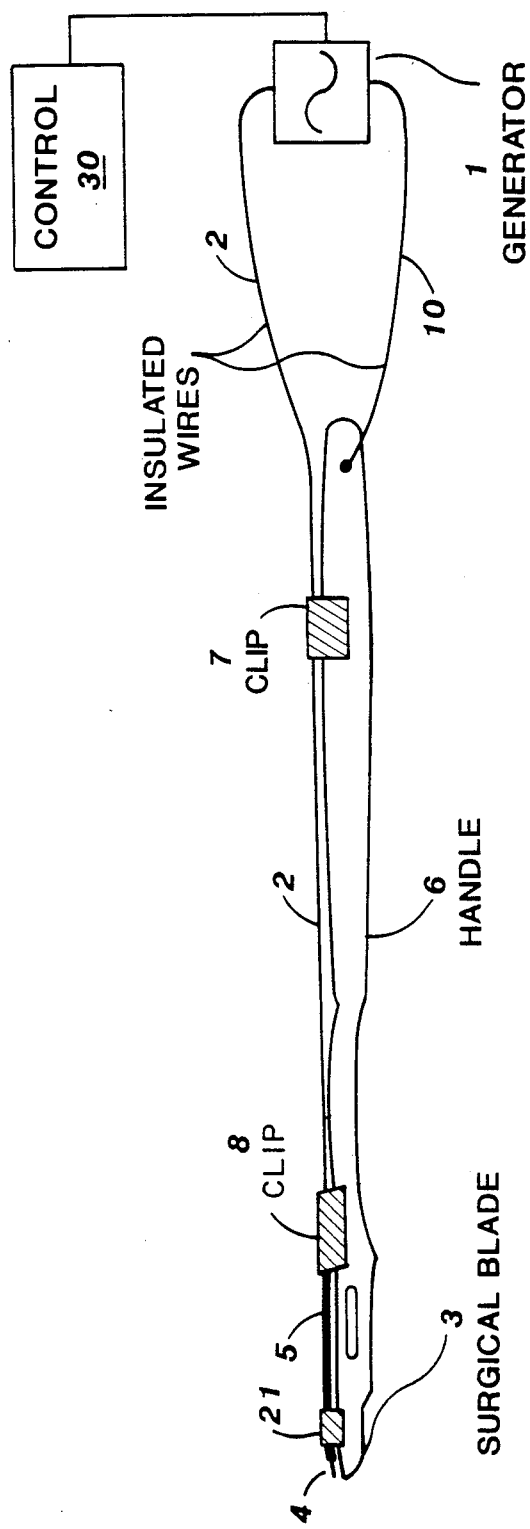
FIG. 3 is a schematic representation of the combination pressure cutting and coagulating instrument of the present invention where the pressure cutting member is a conventional design surgical scalpel.

Two embodiments of the present invention will be described in detail hereinbelow. In the first embodiment, a conventional surgical scalpel serves as one of the two required coagulation electrodes for the bipolar coagulation instrument of our invention. One additional electrode is then required to complete the electrical circuit. In the second embodiment, the two coagulation electrodes are electrically isolated from a conventional surgical scalpel. Although a surgical scalpel is used as the pressure cutting member in both embodiments described, the use of other surgical pressure cutting implements would be apparent to those practicing our invention having ordinary skill in the medical arts.

According to the teachings of the present invention, a surgeon would use the scalpel in the usual manner. If it becomes necessary to coagulate a ruptured blood vessel, the surgeon need only rotate the instrument to position the bipolar electrode pair of either embodiment of the present invention to surround the bleeding vessle and apply radio-frequency power to the electrodes in order to affectuate coagulation. The surgeon is not required to redirect his attention from the field of the operation to perform the two procedures. Tests of our invention on laboratory animals by experienced surgeons have been unqualifiedly successful.

Turning now to the drawings, FIG. 1 shows a schematic representation of one embodiment of the present invention in its most basic form. A surgical blade 3 serves as both electrode and pressure cutting member in this embodiment of the present invention. A second electrode 4 provides the other requisite electrode for the bipolar coagulation function of the combination instrument. A radio-frequency generator 1 provides electrical energy to the electrodes through a pair of wires 2, 10. A separate support 5 for the second electrode which also provides the electrical connection between one of the wires 2 and this electrode may be required depending on the method of attachment of the second electrode to the pressure cutting member. A manually actuated current amplitude control 30 permits the surgeon to apply radio-frequency energy to the instrument when required for coagulating tissue.

FIG. 2 schematically shows the use of the embodiment of our invention described in FIG. 1 for coagulating tissue 16. Current 19 is caused to flow between the electrodes 3, 4 which are placed in the region of a cut or ruptured blood vessel 35 resulting from the action of the pressure cutting member 3 until coagulation occurs.

FIG. 3 shows a more complete schematic representation of the embodiment of the apparatus of the present invention shown in FIG. 1. Shown is the pressure cutting member 3 mechanically and electrically attached to a conventional electrically conducting scalpel handle 6.

Insulated conductor 2 is mechanically attached to the handle 6 by means of insulating fasteners 7, 8. Under fastener 8, and insulated from both the handle 6 and the blade 3 is an electrical connection (not shown) between conductor 2 and the second electrode 4 support 5. Support 5 may be itself supported by an insulated fastener 21. A second electrical connection from the radio-frequency generator 1 to the conducting scalpel handle 6 through wire 10 completes the circuit. Since the scalpel blade 3 is electrically connected to the scalpel handle 6, current can flow through tissue in the manner depicted in FIG. 2. The insulated fasteners 7, 8, 21 additionally serve to fix the distance between the bipolar electrodes 3, 4 and to permit the position of the second electrode 4 to be adjusted relative to the tip of the scalpel blade 3.

Figure 4:
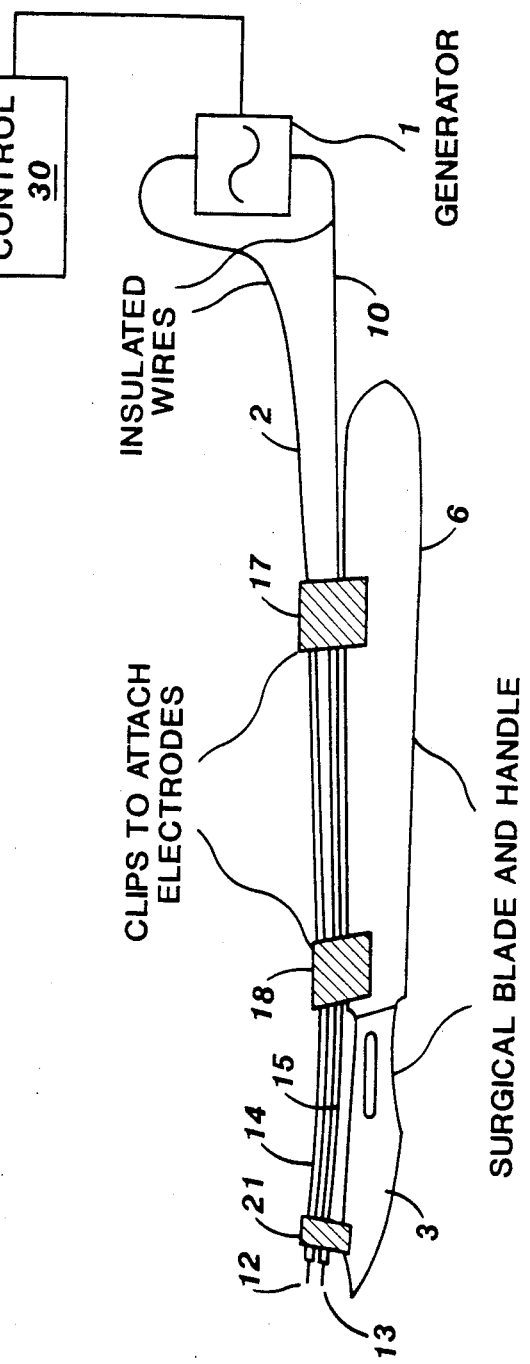
FIG. 4 is a schematic representation of a second embodiment of the present invention where the pressure cutting member is used with a pair of electrodes and is not itself an electrode. Again the pressure cutting member is a conventional design surgical scalpel.

FIG. 4 schematically shows a second embodiment of the present invention. Shown are a pair of electrodes 12, 13 mounted on a scalpel handle 6 using insulated fasteners 17, 18 which serve the additional purpose of permitting the surgeon to slidably change the position of the electrode pair relative to the tip of the surgical blade 3. In this embodiment of our invention, the scalpel blade 3 is not used as an electrode, since the bipolar coagulation apparatus includes electrodes 12 and 13. The spacing between these electrodes is fixed at the optimal distance for coagulation of tissue by fastener 21, and would not be affected by changes in the shape of the surgical blade 3 as would be the embodiment shown in Fig. 3. It should be stressed that both embodiments of our invention could be implemented with conventional surgical instruments without changes having to be made therein.

The foregoing description of two preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What we claim is:

1. A surgical instrument for cutting and coagulating tissue, said surgical instrument comprising in combination:
   means for pressure cutting, said pressure cutting means serving as a first electrode and having a leading edge and a cutting surface, the leading edge of said means for pressure cutting forming the forward portion of the cutting surface;
   second electrode means set apart from and electrically insulated from said pressure cutting means on the side of said pressure cutting means opposite the cutting surface thereof;
   means for attaching said second electrode means to said pressure cutting means; and
   means for providing a voltage between said pressure cutting means and said second electrode means, whereby an electric current can be made to flow between a portion of the side of said pressure cutting means opposite the cutting surface thereof and said second electrode means, and between the leading edge of said pressure cutting means and said second electrode means through tissue which is located therebetween, said current having sufficient amplitude to cause coagulation therein.

2. The apparatus as described in claim 1, wherein said means for providing a voltage between said pressure cutting means and said second electrode means includes a source of radio-frequency voltage.

3. The apparatus as described in claim 2, wherein said second electrode means is located substantially near to the leading edge of said pressure cutting means, whereby coagulation of the tissue placed in contact with said pressure cutting means and said second electrode means can be made to occur substantially immediately after the tissue is acted upon by said pressure cutting means.

4. The apparatus as described in claim 3, wherein said means for attaching said second electrode means permits said second electrode means to be slidably attached to said pressure cutting means, whereby the position of said second electrode means can be adjusted relative to the leading edge of said pressure cutting means.

5. The apparatus as described in claims 1 or 4, wherein said means for providing said voltage between a pressure cutting means and said second electrode means includes manually actuated current amplitude control means.

* * * * *